United States Patent [19]

DeLuca

[11] 4,225,596
[45] Sep. 30, 1980

[54] METHOD FOR TREATING CALCIUM IMBALANCE AND IMPROVING CALCIUM ABSORPTION IN MAMMALS

[75] Inventor: Hector F. DeLuca, Madison, Wis.

[73] Assignee: Wisconsin Alumni Research Foundation, Madison, Wis.

[21] Appl. No.: 951,320

[22] Filed: Oct. 13, 1978

[51] Int. Cl.³ .............................................. A61K 31/59
[52] U.S. Cl. ................................................... 424/236
[58] Field of Search ........................................ 424/236

[56] References Cited

U.S. PATENT DOCUMENTS

| | | | |
|---|---|---|---|
| 3,833,622 | 9/1974 | Babcock et al. | 424/236 |
| 3,880,894 | 4/1975 | DeLuca et al. | 260/397.2 |
| 3,907,843 | 9/1975 | DeLuca et al. | 260/397.2 |
| 4,004,003 | 1/1977 | Babcock et al. | 424/238 |
| 4,022,768 | 5/1977 | Matsunaga et al. | 260/397.2 |
| 4,022,891 | 5/1977 | Takeshita et al. | 424/236 |
| 4,069,321 | 1/1978 | Jones et al. | 424/236 |

OTHER PUBLICATIONS

Science 175, pp. 768–769 (1972), Raisz et al.

Primary Examiner—Douglas W. Robinson
Attorney, Agent, or Firm—Howard W. Bremer

[57] ABSTRACT

A method for treating or preventing metabolic bone disease characterized by loss of bone mass and of improving the calcium balance and calcium absorption of mammals, particularly of women in the post menopausal state, by administering at least one compound having the formulae

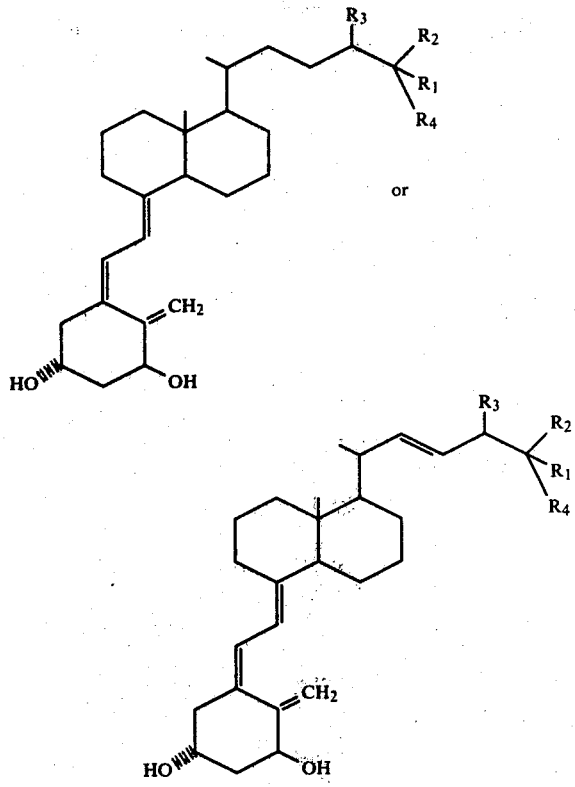

where $R_1$, $R_2$ and $R_4$ are each selected from the group consisting of hydrogen, hydroxyl, lower alkyl, acyl and O-alkyl and $R_3$ is selected from the group consisting of hydrogen, hydroxyl, keto, lower alkyl, acyl and O-alkyl.

5 Claims, No Drawings

METHOD FOR TREATING CALCIUM IMBALANCE AND IMPROVING CALCIUM ABSORPTION IN MAMMALS

The invention described herein was made in the course of work under a grant or award from the Department of Health, Education, and Welfare.

This invention relates to a method for treating metabolic bone disorders characterized by loss of bone mass.

More specifically, this invention relates to a method for improving the calcium balance and calcium absorption in mammals susceptible to or evidencing loss of bone mass.

Still more specifically, this invention relates to a method for treating or for preventing the depletion of calcium from the bones of women entering menopause or who are postmenopausal.

It is well known that females at the time of menopause suffer a marked loss of bone mass giving rise ultimately to osteopenia, which in turn gives rise to spontaneous crush fractures of the vertebrae and fractures of the long bones. This disease is generally known as postmenopausal osteoporosis and presents a major medical problem, both in the United States and most other countries where the life-span of females reaches ages of at least 60 and 70 years. Generally the disease which is often accompanied by bone pain and decreased physical activity, is diagnosed by one or two vertebral crush fractures with X-ray evidence of diminished bone mass. It is known that this disease is accompanied by diminished ability to absorb calcium, decreased levels of sex hormones, especially estrogen and androgen, and a negative calcium balance.

Methods for treating the disease have varied considerably but to date no really satisfactory treatment is yet known. For example, calcium supplementation by itself has not been successful in preventing or curing the disease and the injection of sex hormones, especially estrogen, which has been reported to be effective in preventing the rapid loss of bone mass experienced in postmenopausal women, has been complicated by the fear of its possible carcinogenicity. Other treatments, for which variable results have again been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large amounts of fluoride administered.

It has now been found that in patients showing loss of bone mass with the attendant diminished ability to absorb calcium and a negative calcium balance, the administration of at least one of the compounds of the formulae

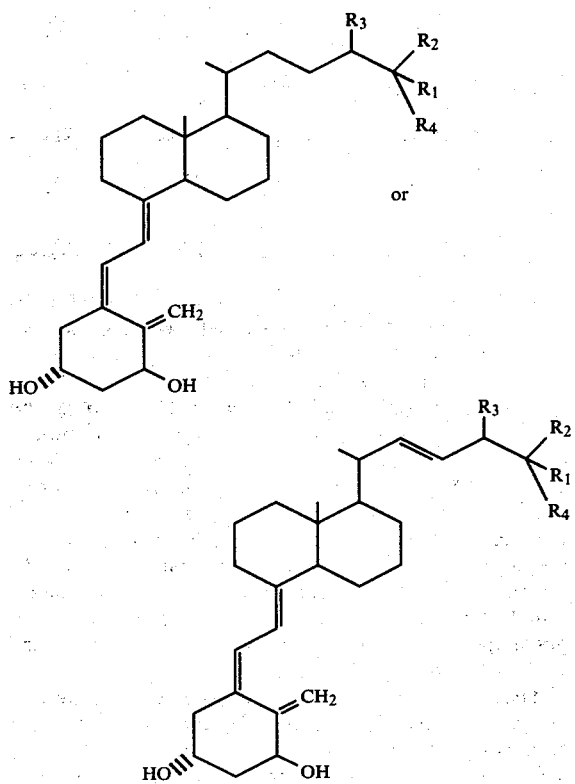

where $R_1$, $R_2$ and $R_4$ are each selected from the group consisting of hydrogen, hydroxyl, lower alkyl, acyl and O-alkyl and $R_3$ is selected from the group consisting of hydrogen, hydroxyl, keto, lower alkyl, acyl and O-alkyl, dramatically improves both the ability to absorb calcium and the calcium balance.

EXAMPLE I

Twenty postmenopausal women were divided into two groups. The division in the two groups was made as a random selection. Thereafter, the groups were coded so that neither the doctors administering the medication not the nurses attending would know what patient might be receiving the compound. All patients had diagnosed loss of bone mass as determined by at least 1 vertebral crush fracture and X-ray evidence of thin bones. Group I received a placebo, which was a capsule containing only a medium chain length triglyceride but having no 1,25-dihydroxycholecalciferol. Group II received the same capsule each day, but containing. 0.5 μg of 1,25-dihydroxycholecalciferol. Prior to entering the study, all patients were equilibrated in the hospital for two weeks and their intake of calcium, their urinary excretion, and fecal excretion were measured. Their net calcium absorption was, therefore, computed by subtracting fecal output from intake. Their net calcium balance was computed by subtracting fecal and urine output from their intake. The results after six months on the described regimen are shown in Table I.

TABLE I

| Improved Calcium Absorption and Balance of Postmenopausal Women Treated with 1,25-dihydroxycholecalciferol for Six Months | | | | | |
|---|---|---|---|---|---|
| Group | Time | Intake (mg) | Urine (mg) | Net Absorption % | Balance (mg) |
| | Before | 677 | 122 | 9.0 | −36 |

TABLE I-continued

Improved Calcium Absorption and Balance of Postmenopausal Women Treated with 1,25-dihydroxycholecalciferol for Six Months

| Group | Time | Intake (mg) | Urine (mg) | Net Absorption % | Balance (mg) |
|---|---|---|---|---|---|
| Placebo | | | | | |
| | After | 688 | 127 | 9.5 | −43 |
| | Before | 759 | 116 | 6.5 | −57 |
| Treated | | | | | |
| | After | 745 | 190 | 26.1 | +1 |

It is clearly evident from the foregoing data that the administration of 1,25-dihydroxycholecalciferol dramatically improves the absorption (intestinal) of calcium as well as the calcium balance.

It is to be understood that although the foregoing Example details the use of 1,25-dihydroxycholecalciferol, other compounds within the scope of the claims can be readily utilized in the treatment of this invention with essentially equivalent results. For example, 1α-hydroxycholecalciferol and 1α-hydroxyergocalciferol are eminently suitable and readily substitutable for the 1,25-dihydroxycholecalciferol. Other compounds which find ready application are 1,25-dihydroxyergocalciferol, 1,24-dihydroxycholecalciferol and 1,24,25-trihydroxycholecalciferol.

These compounds can be administered as sterile parenteral solutions by injection or intravenously or by alimentary canal in the form of oral dosages, or by suppository. Doses of from about one-tenth microgram to about one microgram per day are generally effective to practice the present invention. Although the actual amount of the compound used is not critical, in all cases sufficient of the compound should be used to improve calcium absorption and the calcium balance. Amounts in excess of about one microgram per day are generally unnecessary to achieve the desired results and may not be economically sound practice. In practice the higher doses are used where therapeutic treatment of a disease state is the desired end while the lower doses are generally used for prophylactic purposes.

Dosage forms of the compounds can be prepared by combining them with non-toxic pharmaceutically acceptable carriers as is well known in the art. Such carriers may be either solid or liquid such as, for example, corn starch, lactose, sucrose, peanut oil, olive oil, sesame oil and propylene glycol. If a solid carrier is used the dosage form of the compounds may be tablets, capsules, powders, troches or lozengers. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances or may contain more than one of the compounds specified herein and in the claims in admixture.

Preferred compounds for the practice of this invention can be readily obtained in accordance with the processes of U.S. Pat. Nos. 4,022,768 (1,25-dihydroxycholecalciferol), 3,741,996 (1α-hydroxycholecalciferol), 3,907,843 (1α-hydroxyergocalciferol) and 3,880,894 (1,25-dihydroxyergocalciferol).

Having thus described the invention what is claimed is:

1. A method for increasing the calcium absorption and retention within the body of mammals displaying evidence of, or having a physiological tendency toward, loss of bone mass, which comprises administering internally to said mammals, in a therapeutically effective amount, at least one compound selected from the group consisting of 1α-hydroxycholecalciferol, 1α-hydroxyergocalciferol, 1,25-dihydroxycholecalciferol, 1,25-dihydroxyergocalciferol and 1,24,25-trihydroxycholecalciferol.

2. The method of claim 1 where the compound is administered in an amount from about one-tenth microgram to about one microgram per day.

3. The method of claim 1 wherein the compound, in solution in a liquid vehicle ingestible by and nontoxic to said mammals is administered orally in encapsulated form.

4. The method of claim 1 wherein the compound is administered to women during and subsequent to menopause.

5. The method of claim 1 wherein the compound is administered to women prior to the onset of menopause.

* * * * *